United States Patent [19]

Callingham et al.

[11] Patent Number: 4,743,440

[45] Date of Patent: May 10, 1988

[54] SKIN COMPOSITION

[75] Inventors: Martin Callingham; Dwaipayan Chaudhuri, both of London; Kenneth V. Curry, Camberley; Barry G. Pike, Wokingham; Michael B. Taylor, Old Headington, all of England

[73] Assignee: Lever Brothers Company, New York, N.Y.

[21] Appl. No.: 288,084

[22] Filed: Jul. 29, 1981

Related U.S. Application Data

[63] Continuation of Ser. No. 33,581, Apr. 26, 1979, abandoned, which is a continuation-in-part of Ser. No. 930,780, Aug. 2, 1978, abandoned, which is a continuation of Ser. No. 842,769, Oct. 17, 1977, abandoned, which is a continuation of Ser. No. 520,124, Nov. 1, 1974, abandoned.

[30] Foreign Application Priority Data

Nov. 8, 1973 [GB] United Kingdom ............... 7351815

[51] Int. Cl.⁴ .................. A61K 7/32; A61K 9/12
[52] U.S. Cl. ................................ 424/46; 424/47
[58] Field of Search ............................ 424/46, 47

[56] References Cited

U.S. PATENT DOCUMENTS

| Re. 25,022 | 8/1961 | Spiegel | 424/47 |
|---|---|---|---|
| 2,782,975 | 2/1957 | Bird | 424/46 |
| 3,574,822 | 4/1971 | Shepherd et al. | 424/46 |
| 3,577,516 | 5/1971 | Gould et al. | 424/46 |
| 3,697,644 | 10/1972 | Laiderman | 424/363 |
| 3,764,707 | 10/1973 | Habersberger | 424/363 |
| 3,819,671 | 6/1974 | Bouillon et al. | 424/47 |
| 3,929,986 | 12/1975 | Bouillon et al. | 424/46 |
| 4,012,499 | 3/1977 | Hodson et al. | 424/46 |

FOREIGN PATENT DOCUMENTS

| 569520 | 12/1929 | Fed. Rep. of Germany | 424/363 |
|---|---|---|---|
| 1617850 | 4/1971 | Fed. Rep. of Germany | 424/46 |
| 2503962 | 8/1976 | Fed. Rep. of Germany | 424/46 |
| 1163826 | 5/1958 | France | 424/68 |
| 1218222 | 11/1971 | United Kingdom | 424/46 |
| 1485373 | 9/1977 | United Kingdom | . |
| 1501862 | 2/1978 | United Kingdom | . |

OTHER PUBLICATIONS

Rovesti Article, Les Talcs Orthodermiques in Parfumerie Cosmetique Savons, pp. 276-285 (1965).

*Primary Examiner*—Dale R. Ore
*Attorney, Agent, or Firm*—Milton L. Honig; James J. Farrell

[57] ABSTRACT

A personal antiperspirant product contains a moisture-absorbent polymer instead of or in addition to the usual metal salt. The product is applied to the skin in a finely divided form to give a dry, non-sticky deposit for absorbing skin moisture such as perspiration. The polymer is capable of absorbing an amount of moisture at least equal to its own weight after depositing the product onto the skin.

7 Claims, No Drawings

SKIN COMPOSITION

This application is a continuation of Ser. No. 033,581, filed on Apr. 26, 1979, which is continuation-in-part of Ser. No. 930,780, filed on Aug. 2, 1978, which is a continuation of Ser. No. 842,769, filed Oct. 17, 1977, which is a continuation of Ser. No. 520,124 filed Nov. 1, 1974, all now abandoned.

The invention relates to antiperspirant compositions for dispensing in finely divided form to provide a deposit on human skin. More particularly the invention relates to pressurized antiperspirant compositions which are dispensible from valved aerosol containers and are deposited on the skin in powder form; such compositions are based on moisture-absorbent materials which are generally non-astringent in nature and which help to make the composition non-staining and milder to the skin.

Antiperspirant compositions normally contain an astringent, such as aluminum chlorhydrate or zinc phenol sulphonate, which is believed to depress the formation of perspiration from sweat glands. These astringents are commonly applied to the skin in the form of an aerosol spray.

We have now devised an entirely new type of composition for limiting the manifestation of perspiration on the skin which does not necessarily require the use of astringent perspiration depressants such as those exemplified above and which therefore increases the mildness of the composition by obviating the irritating effect that astringents and their by products can produce. Where mildness is of little consequence, astringent antiperspirant agents can if desired be incorporated in compositions according to the invention. Therefore, instead of relying entirely on chemical suppression of perspiration at source, we employ a means whereby perspiration can be absorbed at the skin surface as soon as it is formed, thus maintaining the skin in an apparently dry condition. This is achieved by spraying or powdering the skin with a composition containing a material having a high capacity for absorbing superficial skin moisture. It follows that transfer of perspiration from the skin to adjacent clothing can also be limited or prevented completely.

Accordingly, the invention provides a fluid antiperspirant composition for dispensing in particulate form onto the human skin to provide a non-toxic, non-irritant, dry to the touch, non-sticky, non-film-forming deposit, the composition comprising a non-aqueous liquid phase and solid phase, the solid phase of the composition comprising from about 1% to about 95% by weight of a moisture-absorbent organic polymer in particulate form, and the non-aqueous liquid phase of the composition comprising (a) from 1% to about 99% by weight of a propellant to produce an aerosol spray, and (b) from 0% to about 99% by weight of a carrier, other than a propellant, for the organic polymer, the organic polymer being characterized by its capacity for absorbing an amount of moisture at least equal to its own weight after deposition of the composition onto the skin.

Compositions according to the invention are fluids and should be prepared and packaged in such a manner that they can be applied to the skin of the user in the form of a spray. A convenient form of packaging is a valved aerosol container for use with conventional liquefiable propellant gases, the valve being adapted to suit the composition and to dispense it as a finely divided spray.

The fluid composition is preferably in the form of a non-aqueous liquid containing a suspension of the moisture-absorbent polymer as a finely divided powder. The polymer can, as a further alternative, be a dry, free-flowing finely divided powder, in a container with sufficient propellant, which when used will dispense the dry powder. The antiperspirant composition according to the invention can also comprise other ingredients in powder form.

An important property of the aerosol antiperspirant composition is that after spraying or otherwise applying it on the skin, it forms a non-toxic, non-irritant, dry to the touch, non-sticky, non-film-forming, moisture absorbent deposit composed essentially of the moisture-absorbent polymer. It is therefore necessary to select the polymer both for its ability to absorb an appreciable amount of water and for its ability to form a dry, non-sticky non-film-forming deposit on the skin.

By "a dry to the touch, non-sticky, non-film-forming deposit" we mean a deposit, which after application to the skin feels dry and is not sticky or tacky to the touch and which does not normally become sticky in use as it absorbs moisture such as perspiration and to which adjacent clothing will not adhere. It will be appreciated that the user is likely to be dissatisfied with an antiperspirant product that remains tacky or sticky after application to the skin and adheres to adjacent clothing. For this reason we do not claim a monopoly for the use of moisture-absorbent organic polymers which are sticky under conditions of use on human skin.

We have found that compositions containing most potentially "non-sticky-in-use" polymers can, however, give rise to an unacceptably sticky deposit if other ingredients, such as oily carriers, are included in the composition in an excessive amount. Care should therefore be taken not to include in the composition excessive amounts of such ingredients.

The antiperspirant composition should, according to a preferred embodiment of the invention, comprise a moisture-absorbent polymer in the form of a powder which is packaged with a propellant. It is understood, however, that the moisture-absorbent polymer may be present in a suitable carrier as a suspension together with a propellant.

Although the average particle size of the powder is usually not critical with respect to its ability to adhere to the skin or to absorb moisture from the skin, it is necessary to ensure that the average particle size is small enough to pass through an aerosol dispensing valve without clogging. It is apparent that the average particle size of the powder and of the valve orifice and packaging dimensions can be selected such that the antiperspirant composition is dispensed without such problems arising.

By way of example only, a suitable average particle size for a moisture-absorbent polymer is not greater than 60 microns, preferably not greater than 30 microns.

The moisture-absorbent organic polymer is a polymer which is organic rather than inorganic in structure and which can be either synthetic or natural in origin which can itself be soluble or insoluble in water, while possessing the necessary ability to absorb water. Whereas the polymer should be capable, when deposited onto human skin following application of the antiperspirant composition, of absorbing from the dry state an amount of water at least equal to its own weight, the preferred polymers are capable of absorbing a greater proportion of water. For example, some polymers after deposition can absorb up to 5 to 10 times their own weight of moisture or even more and still remain on the skin in a dry to the touch, non-sticky, non-film-forming state.

The preferred polymers according to the invention are those which exhibit the greatest capacity for absorbing water, although many of these highly absorbent polymers are costly to produce and hence may be impracticable to use for economic reasons.

Moisture-absorbent polymers for use according to the invention should preferably also have the ability of losing absorbed moisture by evaporation while in contact with the skin, so that they can thereby be self regenerating to a state of increased moisture absorbency and so prolong their antiperspirant effectiveness.

This property of moisture-absorbency can readily be assessed by simply adding water to a deposit of the test polymer on a suitable surface to simulate skin until the deposit appears wet and hence is no longer dry to the touch. The moisture uptake, and also the ability subsequently to lose absorbed moisture by evaporation, can then be assessed gravimetrically.

Moisture-absorbent polymers which we have found to be particularly suitable include certain polysaccharides, polypeptides, vinyl carboxy polymers and copolymers. Examples of the preferred polymers can conveniently be classified as follows:

(a) Water soluble polymers (i) Of natural origin: carragheenates, guar gum, locust bean gum, low methoxy pectins [eg., pages 159-175 of Glicksman, ibid.], agar, furcellaran, xanthan gum, gelatin.

(ii) Of synthetic origin: hydroxyproplymethyl cellulose, sodium carboxymethyl cellulose, polyethylene oxides [eg. pages 495-505 of Glicksman, ibid.], polyvinylpyrrolidone (see Glicksman, ibid. at pages 473-483), carboxyvinyl polymers (such as Carbopol: see Glicksman, ibid. at pages 483 to seq.), copolymers of methyl vinyl ether and maleic anhydrides (as sold under the tradename GANTREZ by the GAF Corporation), linear ionenes [see Reinbaum et al. J. Polymer Science (Polymer Letter), 6, 159-177 (1968)]

(b) Water insoluble polymers (i) Of natural origin: mixed salts of calcium and sodium alginate, crosslinked dextrans, chemically modified cellulose, microcrystalline cellulose, calcium alginate, alginic acid, pregelatinized starches (see Glicksman, supra. at pages 300-301), chemically modified starches (see Glicksman, supra. at pages 310-316), and especially those identified and prepared by the methods set out in U.S. Pat. No. 3,002,823; and starch copolymers such as hydrolyzed (particularly base-hydrolyzed) starch—polyacrylonitrile graft copolymers—especially those graft copolymers identified and prepared by the methods set out in Journal of Applied Polymer Science, Volume 13, pages 2007-2017 (1969), and in Volume 15, pages 3015-3024.

(ii) Of synthetic origin: crosslinked polyacrylamides (see Leonard, "Vinyl and Diene Monomers" Pt I at pages 98-99), crosslinked polacrylic acids (see Glicksman supra. at pages 483-84), crosslinked polyhydroxyethyl methacrylate (see Simpson, "Bio-Medical Engineering" 4, (February 1969) at pages 65-68), crosslinked polyvinyl alcohol (see Warson "Polyvinyl Alcohols and Copolymers", University of Bradford Symposium, 1969), crosslinked polyvinylpyrrolidone (see Glicksman, supra at pages 473-483), sulphonated polystyrene crosslinked with di-vinylbenzene, quaternized polyvinyl pyridine crosslinked with di-vinyl benzene, crosslinked or branched ionenes (see Reinbaum et al., J. Polymer Science (Polymer Letters), I (1969) at pages 295-402).

The proportion of the polymer in the antiperspirant composition according to the invention for dispensing in particulate form such as a spray, will generally depend on the amount of propellant present in the composition, the physical nature of the composition, and on the type of aerosol device employed. Thus, when the antiperspirant composition is a liquid containing powder in suspension and is packaged in the usual single compartment can, then the polymer can form from about 1% to about 30%, preferably from about 3% to about 10% by weight of the composition. On the other hand, when the propellant is largely separated from the antiperspirant composition in a separate compartment within the container, for example such as the device described in U.S. Pat. No. 3,995,778, then the polymer in the composition as dispensed from the container can form up to 95% by weight of the composition.

It is apparent that some organic polymers fulfill the requirement so far as moisture-absorbency is concerned, yet they form a deposit when sprayed onto the skin which remains sticky or which becomes sticky in use. A notable example is sodium alginate, most forms of which can absorb from about 1 to about 12 times their own weight of water under test conditions on human skin. Accordingly, we make no claim to a monopoly for an antiperspirant composition which includes as the sole moisture-absorbing polymer sodium alginate or other organic polymers which behave in a similar manner. It will be appreciated, however, that sodium alginate or like polymers can be incorporated in antiperspirant compositions according to the invention, provided that there is also present a sufficient amount of a "non-sticky" moisture-absorbent polymer to compensate for the undesirable "stickiness" which would otherwise be manifest.

The propellant gas according to the invention can be any liquefiable gas known to the art for use in aerosol containers. Examples of suitable propellants are trichlorofluoromethane (Propellant 11), dichlorodifluoromethane (Propellant 12), dichlorotetrafluoromethane (Propellant 114), monochlorodifluoromethane (Propellant 22), trichlorotrifluoromethane (Propellant 113), propane, butane and isobutane used singly or in admixture. See also Sanders, "Principles of Aerosol Technology" (1970), pages 3-4, 18-28 and U.S. Pat. No. 3,792,068. Trichlorofluoromethane, dichlorodifluoromethane, dichlorotetrafluoromethane and isobutane used singly or admixed are preferred propellants. Selection of appropriate amounts of the propellant gas or gas mixture is governed by normal testing as well known in the aerosol art. Although the composition according to the invention in its simplest form can consist of a suspension of the moisture-absorbent polymer in propellant, the propellant thus functioning as a carrier, generally it is satisfactory to consider the propellant as constituting the balance of the antiperspirant composition that is not accounted for by the other components disclosed hereinbefore and hereinafter. Generally, the propellant constitutes from about 1% to about 99% by weight of the antiperspirant composition. Especially preferred limits of propellant when the usual single compartment aerosol container is used are from about 40% to about 95% by weight of the composition. With special containers where most of the propellant is kept separate from the product to be dispensed, such as for example the two compartment container described in U.S. Pat. No. 3,995,778, the preferred limits of propellant are from about 1% to about 50%, most preferably from 1% to 10% by weight of the composition.

It is also possible to incorporate in the antiperspirant composition according to the invention, a cosmetically acceptable carrier which can function in a variety of ways in improving the effectiveness of the composition. In particular, the presence of a carrier can improve initial adhesion of the moisture-absorbent polymer to the skin, thus aiding in its "capture" by the skin as it is dispensed in spray form. Also, a carrier can function as a diluent, lubricant or as a spreading agent to facilitate uniform distribution of the moisture-absorbent polymer on the skin.

In the case where the fluid antiperspirant composition is in the form of a suspension of a liquid containing a powder, a carrier such as, isopropyl myristate, hexylene glycol, dipropylene glycol, ethanol or other alcohols such as poly-lower alkoxylated cetyl alcohols, or esters such as di-n-butylphthalate, diethyl sebacate, di-isopropyl adipate and o-ethyl, ethyl-carboxymethyl phthalate and mixtures thereof, is particularly effective in improving the adherence of the moisture-absorbent polymer to the skin.

The amount of carrier, when present in the antiperspirant composition, according to the invention herein, can form up to about 99% by weight of the total composition. The preferred level of carrier is from about 1% to about 50%, most preferably from about 5% to about 20% by weight of the total composition. Above about 20%, the composition deposited on the skin can feel undesirably sticky, tacky, oily or greasy, depending on the nature of the carrier.

It may be necessary to include a suspending agent in the aerosol antiperspirant composition to prevent the moisture-absorbent powder from settling out. There is a wide range of suitable commercially available suspending agents. Examples of such suspending agents include hydrophobic treated clays that swell in organic solvents, an example of which is hydrophobic bentonite, such as Bentone 38, pyrogenic silicas such as Cab-O-Sil M-5 and AEROSIL 200 and grease-forming soaps such as aluminum stearate. Another class of suspending agents which optionally can be used are monoethanolamides such as coconut monoethanolamide, octadecylmonoethanolamide and stearoyl monoethanolamide. Yet another class of suspending agents are amines such as lauryl amine, stearyl amine, tetradecyl amine, hexadecyl amine, octadecylamine and eicosyl amine.

The suspending agent when employed is generally of colloidal dimensions having a particle size of less than 0.03 microns. The suspending agent can be present in the composition in an amount of up to 2%, preferably 0.1 to 1.5% by weight of the composition.

In addition to the ingredients of the composition as set out hereinbefore, minor ingredients can optionally also be included. As an example, germicides can be incorporated in the antiperspirant composition. Suitable germicides, by way of example only, are trichlorocarbanilide, trifluoromethylcarbanilide, tribromosalicylanilide and 2,4,4'trichloro-2-hydroxydiphenyl ether.

Such germicides when used can be employed in an amount of up to about 0.5% by weight of the composition in order to inhibit the proliferation of skin bacteria and reduce or prevent the development of unpleasant odors.

It is also possible optionally to include a perfume and/or an odor suppressor such as those disclosed in British Patent specification No. 1,472,536 in the antiperspirant composition, usually at a concentration in the composition of no more than about 1% by weight.

As we have stated, it is also possible to incorporate as a further optional ingredient, an effective amount of a perspiration depressant such as, for example, aluminum chlorhydrate, aluminum chloroalcoholates, zinc phenol sulphonate, zirconium halide hydrates and tetraphenyl boron.

Such antiperspirant agents when used can be employed in an amount of up to about 5% by weight of the composition. Usually, when present, these agents form from 0.1 to 1% by weight of the composition.

It is also possible to include in antiperspirant compositions according to the invention anticholinergic agents such as trimethylacetyl scopalamine hydrochloride.

In order to function as an antiperspirant, the composition is sprayed onto the skin, for example the arm pit of the user, so as to provide a non-sticky, moisture-absorbent, non-film-forming deposit on the skin. The moisture-absorbent polymer then functions to absorb moisture as it is secreted from the skin in the form of perspiration so that adjacent clothing is protected, at least for a limited time; from contact with perspiration. This period of protection will depend on the capacity of the polymer to absorb moisture and its loading on the skin, as well as the rate at which the user produces perspiration. Clearly it is, as we have stated, an advantage if the polymer can lose moisture by evaporation while on the skin, so that its effectiveness as an antiperspirant can be prolonged. Accordingly, a method is provided for eliminating perspiration from the human skin by applying thereto an effective amount of the composition defined herein.

The invention is illustrated by the following Examples.

EXAMPLE 1

This Example illustrates the use of a synthetic water-insoluble polymer. The following ingredients were filled into an aerosol container to provide product A:

|  | % by weight |
|---|---|
| Microcrystalline cellulose (AVICEL RC 581) | 3.0 |
| Isopropyl myristate | 3.0 |
| Pyrogenic silica (AEROSIL 200) | 0.2 |
| Perfume | 0.2 |
| Propellant 11/12 (65:35) | to 100 |

A second product (B) was prepared from the same ingredients except that the AVICEL RC581 was replaced by 3.5% by weight of aluminum chlorhydrate.

A panel of 24 testers, all of whom were regular users of aerosol antiperspirants, were asked to assess the two formulations for inhibit on of underarm wetness.

The technique was to spray each of the products onto the freshly washed axillae from a distance of 15 cm for two seconds. This was sufficient time to form, in the case of product A a deposit of the moisture-absorbent polymer (AVICEL RC581) which acted to avoid transfer of perspiration from axillae to adjacent clothing.

The panellists were asked to pursue their normal day to day laboratory work and to assess after five hours the effectiveness of each product by considering the statement: "STOPS UNDERARM WETNESS". For this assessment their answers were marked on a five point scale ranging from 1 (disagree strongly) to 5 (agree strongly). Their scores were then subjected to a statistical analysis to determine overall whether each product as deposited on the skin stopped the development of underarm wetness.

In this particular experiment, formulations A and B each stopped underarm wetness with approximately equal efficacy, thus showing that the traditional antiperspirant property of aluminum chlorhydrate could be totally replaced without loss of efficiency by a moisture-absorbing non-astringent polymer.

The comparison was repeated using two products based on the formulation described above except that in one instance half of the AVICEL RC581 on a weight basis was replaced by sodium alginate to give product C and in the other instance all of the AVICEL RC581 was replaced by an equal weight percent of sodium alginate to give product D.

In this comparison, product D, although initially providing an apparently dry deposit became sticky to the touch within one hour under similar test conditions to that applied to products A and B. Product C, on the other hand, remained dry on the skin and satisfactorily absorbed perspiration over the 5 hour test period without becoming sticky or wet.

It was concluded from this latter comparison that although sodium alginate as a polymer was capable of effectively absorbing perspiration, it became unacceptably sticky under conditions of use. When, however, sodium alginate was mixed with the "non-sticky" polymer, i.e. AVICEL RC581, moisture-absorbency of the product was satisfactory without development of stickiness.

It was concluded that when tested on human subjects, compositions according to the present invention proved to be efficient antiperspirants in that they effectively prevented the appearance of perspiration where deposited on the skin and also on adjacent clothing: there was therefore no clothes staining problem such as is sometimes associated with the use of conventional antiperspirants. The antiperspirant composition according to the invention were also non-irritant.

EXAMPLE 2

An antiperspirant composition according to the invention was prepared from the following ingredients:

|  | % by weight |
| --- | --- |
| Calcium sodium alginate (having a molar ratio of calcium to sodium in the molecule of 1:1) | 5.0 |
| Isopropyl palmitate | 1.0 |
| Ethyl alcohol | 1.8 |
| Perfume | 0.2 |
| Pyrogenic silica (Cab-O-Sil M-5) | 0.4 |
| Polypropoxylated cetyl alcohol | 3.8 |
| Propellant mixture 11/12 (65:35) | to 100 |

The composition was prepared by adding each of the ingredients to a valved aerosol container capable of being pressurized through the valve thereof, sealing the container and then adding propellant mixture to it under pressure through the valve so as to obtain a final pressure of 50 psig. On actuation of the dispensing valve a uniform spray was obtained and it was possible to obtain a fine powder deposit when directed to the skin.

The composition was tested by a trained panel of assessors in the manner described in Example 1. The panel reported that the composition absorbed moisture very well and even after five hours, there was no visible or tactile evidence that perspiration was present: it had been successfully absorbed by the deposit on the skin of calcium sodium alginate.

EXAMPLE 3

The procedure of Example 2 was repeated using calcium sodium alginate having various molar ratios of calcium to sodium.

Each composition was examined for its ability to absorb moisture which remained substantially dry to the touch and non-sticky under conditions of use by human volunteers.

The following table identifies the types of calcium alginate tested and records the moisture-absorbency of each one.

| Calcium, sodium alginate (ratio of Ca:Na) | Ratio of polymer: water at maximum absorbency on skin while remaining dry to the touch |
| --- | --- |
| 1:1 | 5.0 |
| 2:1 | 4.0 |
| 3:1 | 3.0 |
| Calcium alginate | 2.0 |

EXAMPLE 4

A further series of polymers and polymeric mixtures was tested as described in Example 3.

The respective degrees of absorbency recorded were as follows:

| Polymer/polymeric mixture | Weight ratios of each ingredient | Ratio of total polymer: water at maximum absorbency on the skin while remaining dry to the touch |
| --- | --- | --- |
| Calcium sodium alginate (1:1) + micro-crystalline cellulose (AVICEL RC581) | 5:1 | 4.5 |
| Calcium sodium alginate (2:1) + aluminum magnesium silicate (VEEGUM F) | 5:1 | 5.0 |
| Sodium alginate + micro-crystalline cellulose (AVICEL RC581) | 5:1 | 4.0 |
| Calcium alginate | — | 2.0 |
| Sodium alginate* | — | 4.5 |

*Sodium alginate was only tested for comparison of its moisture absorbency property. In use it produced a skin deposit which was sticky and therefore unacceptable unless mixed with another moisture-absorbent polymer such as is exemplified in this table.

EXAMPLE 5

An antiperspirant composition containing two moisture absorbers was prepared according to the method described in Example 2 from the following ingredients:

| | % by weight |
|---|---|
| Calcium sodium alginate (1:1) | 3.5 |
| Microcrystalline cellulose (AVICEL RC581) | 1.5 |
| Isopropyl myristate | 4.5 |
| Nonionic detergent | 0.1 |
| Pyrogenic silica (AEROSIL 200) | 0.4 |
| Perfume | q.s. |
| Propellant mixture 11/12 (65:35) | to 100 |

EXAMPLE 6

An antiperspirant composition containing a germicide was prepared according to the method described in Example 2 from the following ingredients:

| | % by weight |
|---|---|
| Cross-linkd polyacrylic acid | 5.0 |
| Isopropyl myristate | 4.5 |
| Nonionic detergent | 0.1 |
| 2,4,4'-trichloro-2-hydroxy-diphenyl ether (Irgasan DP300) | 0.5 |
| Pyrogenic silica (AEROSIL 200) | 0.4 |
| Perfume | q.s. |
| Propellant mixture 11/12 (65:35) | to 100 |

EXAMPLE 7

An antiperspirant composition containing a high level of astringent was prepared according to the method described in Example 2 from the following ingredients:

| | % by weight |
|---|---|
| Base-hydrolyzed starch poly-acrylonitrile graft copolymer | 1.5 |
| Aluminum chlorhydrate | 3.5 |
| Isopropyl myristate | 4.5 |
| Nonionic detergent | 0.1 |
| Pyrogenic silica (AEROSIL 200) | 0.4 |
| Perfume | q.s. |
| Propellant mixture 11/12 (65:35) | to 100 |

EXAMPLE 8

An antiperspirant composition containing a low level of aluminum chlorhydrate was prepared according to the method described in Example 2 from the following ingredients:

| | % by weight |
|---|---|
| Cross-linked dextran (SEPHADEX) | 4.5 |
| Aluminum chlorhydrate | 0.5 |
| Isopropyl myristate | 4.5 |
| Nonionic detergent | 0.1 |
| Pyrogenic silica (AEROSIL 200) | 0.4 |
| Perfume | q.s. |
| Propellant mixture 11/12 (65:35) | to 100 |

In the compositions of Examples 5, 6, 7 and 8 which produce excellent powdered antiperspirants dispensable from an aerosol container of the type described in Example 1, various modifications in proportions and constituents were made in accordance with the teachings of the present specification, with satisfactroy antiperspirant compositions resulting.

EXAMPLE 9

A propellant based antiperspirant composition was prepared by mixing together the following ingredients and filling into an aerosol container in the usual manner:

| | % by weight |
|---|---|
| Microcrystalline cellulose (AVICEL RC581) | 22.5 |
| Calcium sodium alginate (2:1) | 22.5 |
| Propellant mixture 11/12 65:35 | 55.0 |

EXAMPLE 10

An aerosol antiperspirant compositon was prepared by blending together the following ingredients:

| | % by weight |
|---|---|
| Calcium sodium alginate (1:1) | 25.0 |
| Pyrogenic silica (AEROSIL 200) | 3.0 |
| 2-ethyl-1,3-hexane diol | 5.0 |
| Perfume | q.v. |
| Industrial Methylated Spirit | to 100 |

This mixture was filled into an aerosol container and after fitting the valve, the container was pressurized with an equal weight of a liquefied propellant mixture (65:35) of 11 and 12 respectively.

What is claimed is:

1. A substantially non-aqueous fluid antiperspirant composition consisting essentially of a solid phase and a non-aqueous liquid phase for dispensing as a spray onto human skin to provide a non-toxic, non-irritant, dry-to-the-touch, non-sticky deposit, the solid phase of the composition comprising from about 1% to about 95% by weight of chemically modified cellulose in particulate form, and the non-aqueous liquid phase of the composition comprising:
(a) from 1% to about 99% by weight of a liquefied propellant to produce an aerosol spray; and
(b) from 0% to 99% by weight of a carrier, other than a propellant, for the chemically modified cellulose, the chemically modified cellulose being characterized by its capacity for absorbing an amount of moisture at least equal to its own weight after deposition of the composition onto the skin.

2. A substantially non-aqueous fluid antiperspirant composition consisting essentially of a solid phase and a non-aqueous liquid phase for dispensing as a spray onto human skin to provide a non-toxic, non-irritant, dry-to-the-touch, non-sticky deposit, the solid phase of the composition comprising from about 1% to about 95% by weight of a moisture-absorbent organic polymer in particulate form, and the non-aqueous liquid phase of the composition comprising:
(a) from 1% to about 99% by weight of a liquefied propellant to produce an aerosol spray; and
(b) from 0% to 99% by weight of a carrier, other than a propellant, for the organic polymer, the organic polymer being characterized by its capacity for absorbing an amount of moisture at least equal to its own weight after deposition of the composition onto the skin, wherein the polymer is a water-soluble polymer of natural origin of carragheenates, guar gum, locust bean gum, low methoxy pectins, agar, furcellaran, xanthan gum, gelatin or mixtures thereof.

3. A substantially non-aqueous fluid antiperspirant composition consisting essentially of a solid phase and a non-aqueous liquid phase for dispensing as a spray onto human skin to provide a non-toxic, non-irritant, dry-to-the-touch, non-sticky deposit, the solid phase of the composition comprising from about 1% to about 95% by weight of a moisture-absorbent organic polymer in particulate form, and the non-aqueous liquid phase of the composition comprising:

(a) from 1% to about 99% by weight of a liquefied propellant to produce an aerosol spray; and (b) from 0% to 99% by weight of a carrier, other than a propellant, for the organic polymer, the organic polymer being characterized by its capacity for absorbing an amount of moisture at least equal to its own weight after deposition of the composition onto the skin, wherein the polymer is a water-soluble polymer of synthetic origin of hydroxypropylmethyl cellulose, sodium carboxymethyl cellulose, polyethylene oxides, polyvinylpyrrolidone, carboxyvinyl polymers, copolymers of methyl vinyl ether and maleic anhydrides, linear ionenes or mixtures thereof.

4. A substantially non-aqueous fluid antiperspirant composition consisting essentially of a solid phase and a non-aqueous liquid phase for dispensing as a spray onto human skin to provide a non-toxic, non-irritant, dry-to-the-touch, non-sticky deposit, the solid phase of the composition comprising from about 1% to about 95% by weight of a cross-linked polyacrylic acid in particulate form, and the non-aqueous liquid phase of the composition comprising:

(a) from 1% to about 99% by weight of a liquefied propellant to produce an aerosol spray; and (b) from 0 to 99% by weight of a carrier, other than a propellant, for the cross-linked polyacylic acid, the cross-linked polyacrylic acid being characterized by its capacity for absorbing an amount of moisture at least equal to its own weight after deposition of the composition onto the skin.

5. A substantially non-aqueous fluid antiperspirant composition consisting essentially of a solid phase and a non-aqueous liquid phase for dispensing as a spray onto human skin to provide a non-toxic, non-irritant, dry-to-the-touch, non-sticky deposit, the solid phase of the composition comprising from about 1% to about 95% by weight of starch-polyacrylonitrile graft copolymers in particulate form, and the non-aqueous liquid phase of the composition comprising:

(a) from 1% to about 99% by weight of a liquefied propellant to produce an aerosol spray; and (b) from 0% to 99% by weight of a carrier, other than a propellant, for the starch-polyacrylonitrile graft copolymers, the starch-polyacrylonitrile graft copolymers being characterized by its capacity for absorbing an amount of moisture at least equal to its own weight after deposition of the composition onto the skin.

6. The fluid antiperspirant composition defined in claim 4, wherein the cross-linked polyacrylic acid absorbs an amount of moisture at least equal to 10 times its own weight.

7. The fluid antiperspirant composition defined in claim 5, wherein the starch-polyacrylonitrile graft copolymer absorbs an amount of moisture at least equal to 10 times its own weight.

* * * * *